(12) United States Patent
Shechter

(10) Patent No.: US 9,031,298 B2
(45) Date of Patent: May 12, 2015

(54) UNDER-SAMPLED, MULTI-ENERGY COMPUTED TOMOGRAPHY (CT) DATA ACQUISITION DATA PROCESSING

(75) Inventor: Gilad Shechter, Haifa (IL)

(73) Assignee: Koninklijke Philips N.V., Eindhoven (NL)

( * ) Notice: Subject to any disclaimer, the term of this patent is extended or adjusted under 35 U.S.C. 154(b) by 171 days.

(21) Appl. No.: 13/879,817

(22) PCT Filed: Oct. 26, 2011

(86) PCT No.: PCT/IB2011/054782
§ 371 (c)(1),
(2), (4) Date: Apr. 17, 2013

(87) PCT Pub. No.: WO2012/056412
PCT Pub. Date: May 3, 2012

(65) Prior Publication Data
US 2013/0202178 A1  Aug. 8, 2013

Related U.S. Application Data

(60) Provisional application No. 61/407,039, filed on Oct. 27, 2010.

(51) Int. Cl.
| G06K 9/00 | (2006.01) |
| G06T 7/00 | (2006.01) |
| A61B 6/03 | (2006.01) |
| A61B 6/00 | (2006.01) |
| G01N 23/04 | (2006.01) |
| G06T 11/00 | (2006.01) |

(52) U.S. Cl.
CPC ............... *G06T 7/0004* (2013.01); *A61B 6/032* (2013.01); *A61B 6/4035* (2013.01); *A61B 6/482* (2013.01); *A61B 6/5205* (2013.01); *A61B 6/5258* (2013.01); *G01N 23/046* (2013.01); *G06T 11/005* (2013.01); *G06T 2211/408* (2013.01); *G01N 2223/419* (2013.01)

(58) Field of Classification Search
USPC ................. 250/363.04; 278/21–27; 382/131; 424/9.4
See application file for complete search history.

(56) References Cited

U.S. PATENT DOCUMENTS 7,298,812 B2    11/2007   Tkaczyk et al.
2009/0092219 A1  4/2009   Wu et al.
(Continued)

OTHER PUBLICATIONS

Joel Larsson, "The Use of Dual-Energy in Computer Tomography" Jun. 21, 2010, Retrieved from the Internet on Dec. 11, 2014, Retrieved from URL:<http://www.radfys.gu.se/digitalAssets/1312/1312301_joel-larsson-thesis.pdf>.*
(Continued)

*Primary Examiner* — Gregory F Cunningham

(57) ABSTRACT

A method includes extracting a fully sampled fixed kVp sinogram for a pre-determined kVp of interest from an under-sampled mixed kVp sinogram generated from a switched kVp computed tomography scan. A system includes a fixed sinogram extractor that extracts a fully sampled fixed kVp sinogram from an under-sampled mixed kVp sinogram from a switched kVp computed tomography scan. A method includes de-noising at least one of a fully sampled fixed kVp sinogram extracted from an under-sampled mixed kVp sinogram or the under-sampled mixed kVp sinogram by smoothing lower kVp measurements of the sinograms and sharpening higher kVp measurements of the sinograms.

28 Claims, 4 Drawing Sheets

(56) References Cited

U.S. PATENT DOCUMENTS

Figure 1:
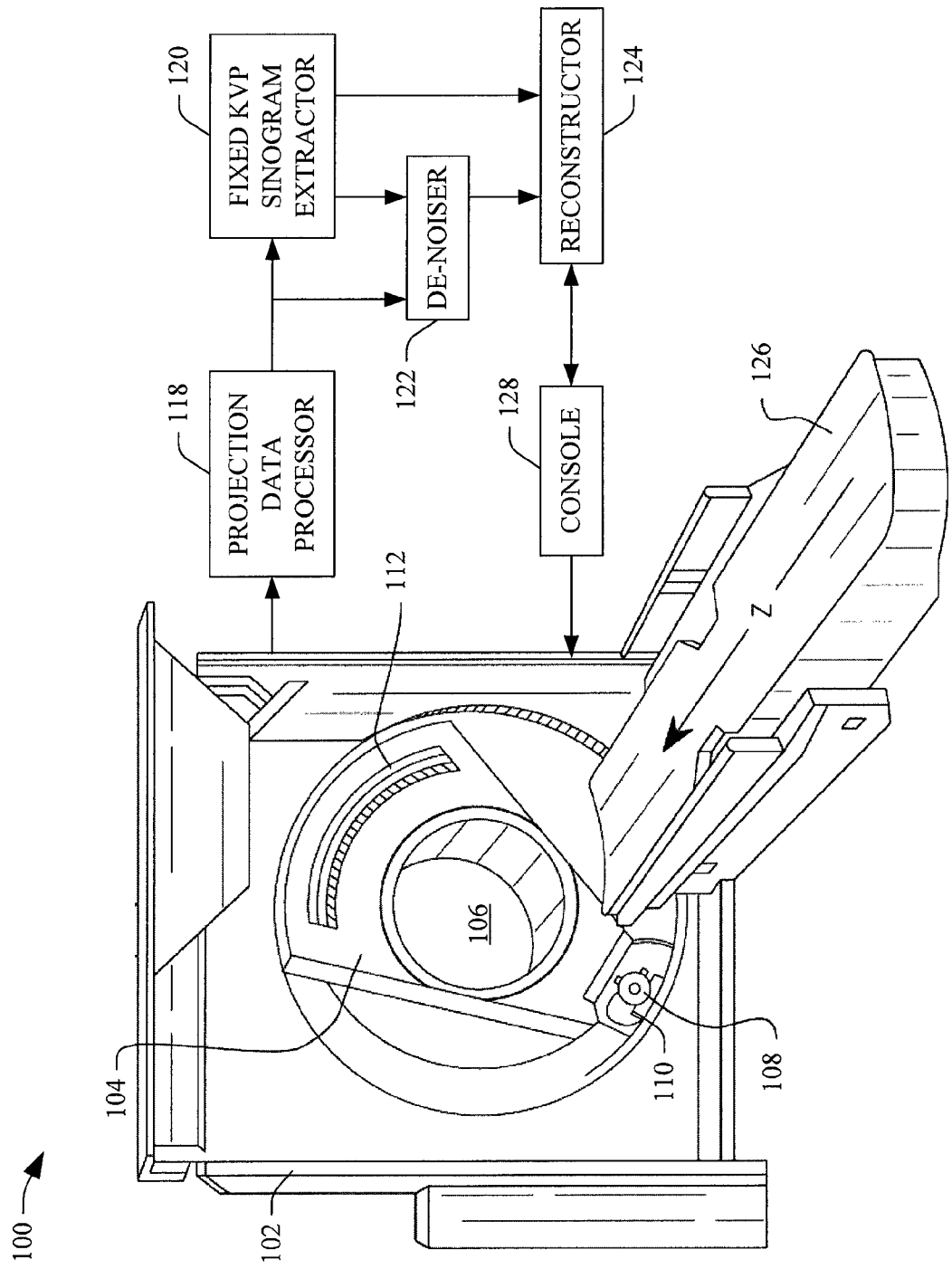

| | | |
|---|---|---|
| 2009/0097611 A1* | 4/2009 | Nishide et al. .................... 378/5 |
| 2009/0207966 A1 | 8/2009 | Shkumat et al. |
| 2010/0104062 A1 | 4/2010 | Wu et al. |
| 2010/0239143 A1* | 9/2010 | Griswold et al. ............. 382/131 |
| 2012/0114093 A1* | 5/2012 | Yu et al. ........................... 378/8 |

OTHER PUBLICATIONS

Joel Larsson, "The Use of Dual-Energy in Computer Tomography" Jun. 21, 2010, Retrieved from the Internet on Dec. 11, 2014, Retrieved from U RL: /www.radfys.gu.se/digitalAssets/1312/131230 1joel-larsson-thesis.pdf>.*

Hounsfield, G. N.; Computerized transverse axial scanning (tomography): Part I. Description of system; 1973; British Journal of Radiology; 46:1016-1022.

Huh, W., et al.; Fast KVP-Switching Dual energy CT for PET Attenuation Correction; 2009; IEEE Nuclear Science Symposium Conference Record; pp. 2510-2515.

Noh, J., et al.; Statistical Sinogram Restoration in Dual-Energy CT for PET Attenuation Correction; 2009; IEEE Trans. on Medical Imaging; 28(11)1688-1702.

Szczykutowscz; T., et al.; Spectral CT Imaging using a Slow kVp switching Technique and PICCS Image Reconstruction; 2010; Proc. of First Intl. Mtg. on Image Formation in x-Ray CT; pp. 14-17.

Smith, C. R., et al.; Application of 450 kV Computed Tomography to Engine Blocks with Steel Liners; 2007; Materials Evaluation; 65(5)458-461.

* cited by examiner

UNDER-SAMPLED, MULTI-ENERGY COMPUTED TOMOGRAPHY (CT) DATA ACQUISITION DATA PROCESSING

CROSS REFERENCE TO RELATED APPLICATIONS

This application is a national filing of PCT application Serial No. PCT/IB2011/054782, filed Oct. 26, 2011, published as WO 2012/056412 A1 on May 3, 2012, which claims the benefit of U.S. provisional application Ser. No. 61/407,039 filed Oct. 27, 2010, which is incorporated herein by reference.

The following generally relates to computed tomography (CT) and more particularly to determining fully sampled sinograms at a plurality of fixed kVp values from an under-sampled, multi-energy, kVp switching computed tomography (CT) data acquisition, and processing the fixed kVp sinograms and/or the original mixed kVp sinogram to reduce noise without reducing spatial resolution.

A computed tomography (CT) scanner includes an x-ray tube that emits radiation that traverses an examination region and a portion of an object or subject therein. With dual-energy CT, the emission spectrum of the tube is switched between at least two different emission spectrums. A detector detects radiation traversing the examination region and generates projection data indicative of the detected radiation. A reconstructor reconstructs the projection data and generates volumetric image data indicative of the portion of the object or subject in the examination region. An image processor can be used to generate one or more anatomical images and/or spectral separation images from the volumetric image data.

One approach to switching the emission spectrum of the tube is to switch the tube voltage between two different energy levels ("kVp switching"). Unfortunately, kVp switching causes both the lower energy data acquisition data and the higher energy data acquisition data to be under-sampled. As a consequence, streak artifact may be introduced into the anatomical images and in the images used for spectral separation.

In addition, due to the variation of photon statistics between integration periods (IP) at higher and lower kVp levels, the dose required for obtaining either the anatomical images or the spectral separation images, at given resolution and noise levels, increases relative to the dose for a fixed kVp data acquisition. In other words, the variation of photon statistics between different integration periods (IP) reduces the overall dose utility, or requires a higher patient dose for given image resolution and noise levels.

Aspects of the present application address the above-referenced matters and others.

According to one aspect, a method includes extracting a fully sampled fixed kVp sinogram for a pre-determined kVp of interest from an under-sampled mixed kVp sinogram generated from a switched kVp computed tomography scan.

According to another aspect, a method includes a fixed sinogram extractor that extracts a fully sampled fixed kVp sinogram from an under-sampled mixed kVp sinogram from a switched kVp computed tomography scan.

According to another aspect, a method includes de-noising at least one of a fully sampled fixed kVp sinogram extracted from an under-sampled mixed kVp sinogram or the under-sampled mixed kVp sinogram by smoothing lower kVp measurements of the sinograms and sharpening higher kVp measurements of the sinograms.

The invention may take form in various components and arrangements of components, and in various steps and arrangements of steps. The drawings are only for purposes of illustrating the preferred embodiments and are not to be construed as limiting the invention.

Figure 2:
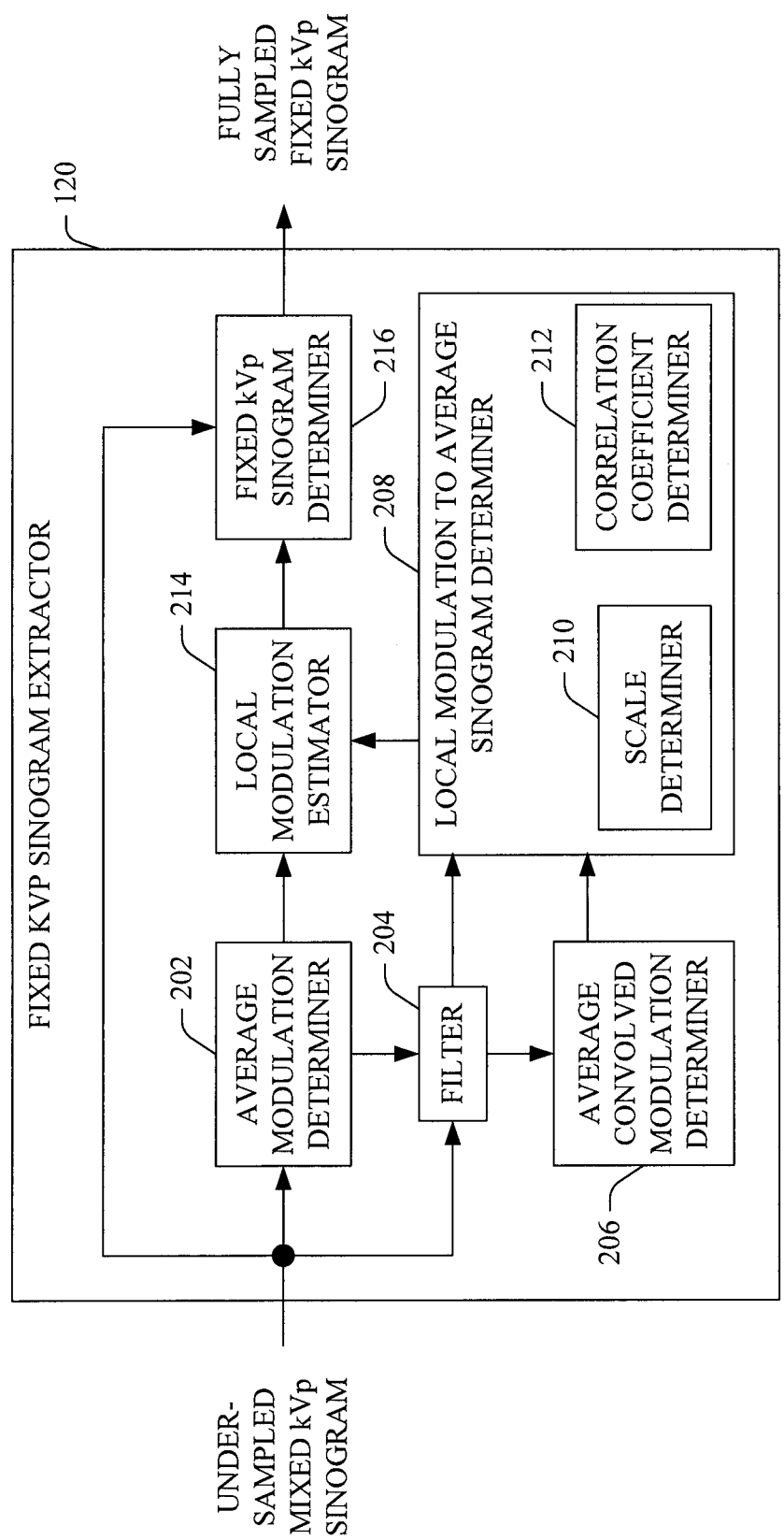
Figure 3:
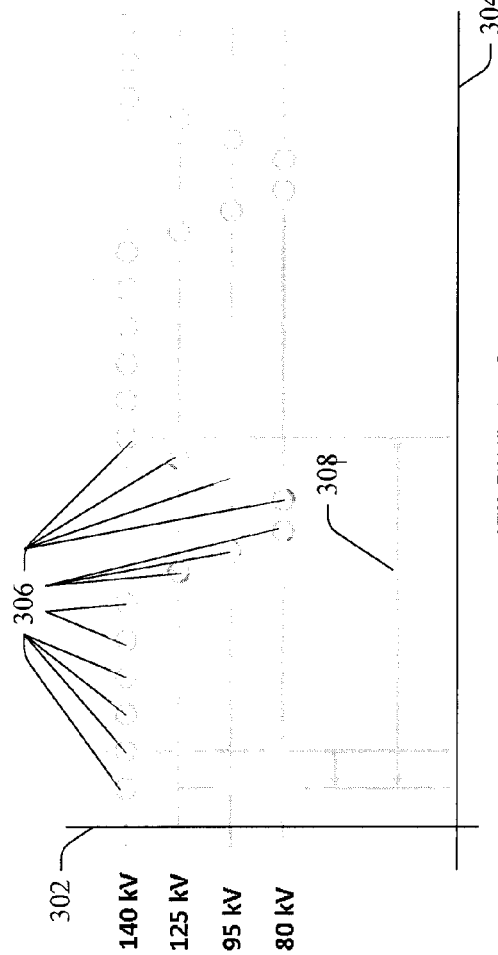
Figure 4:
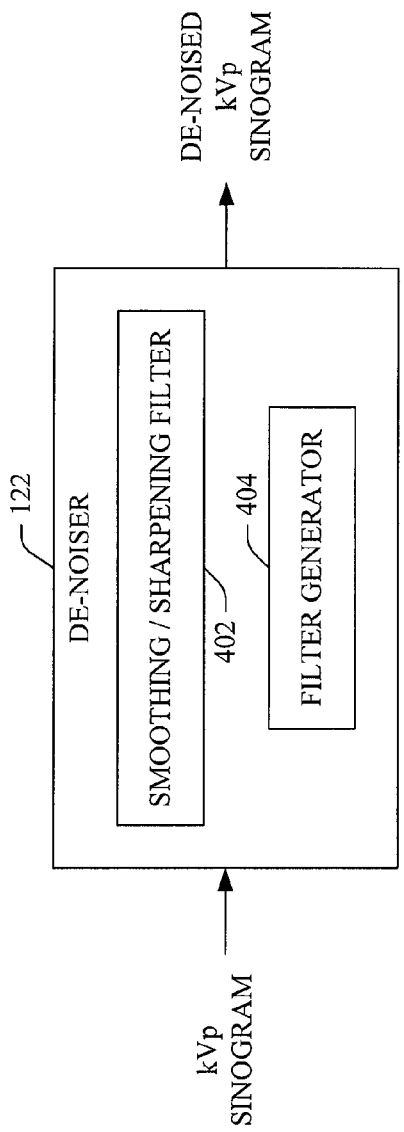
Figure 5:
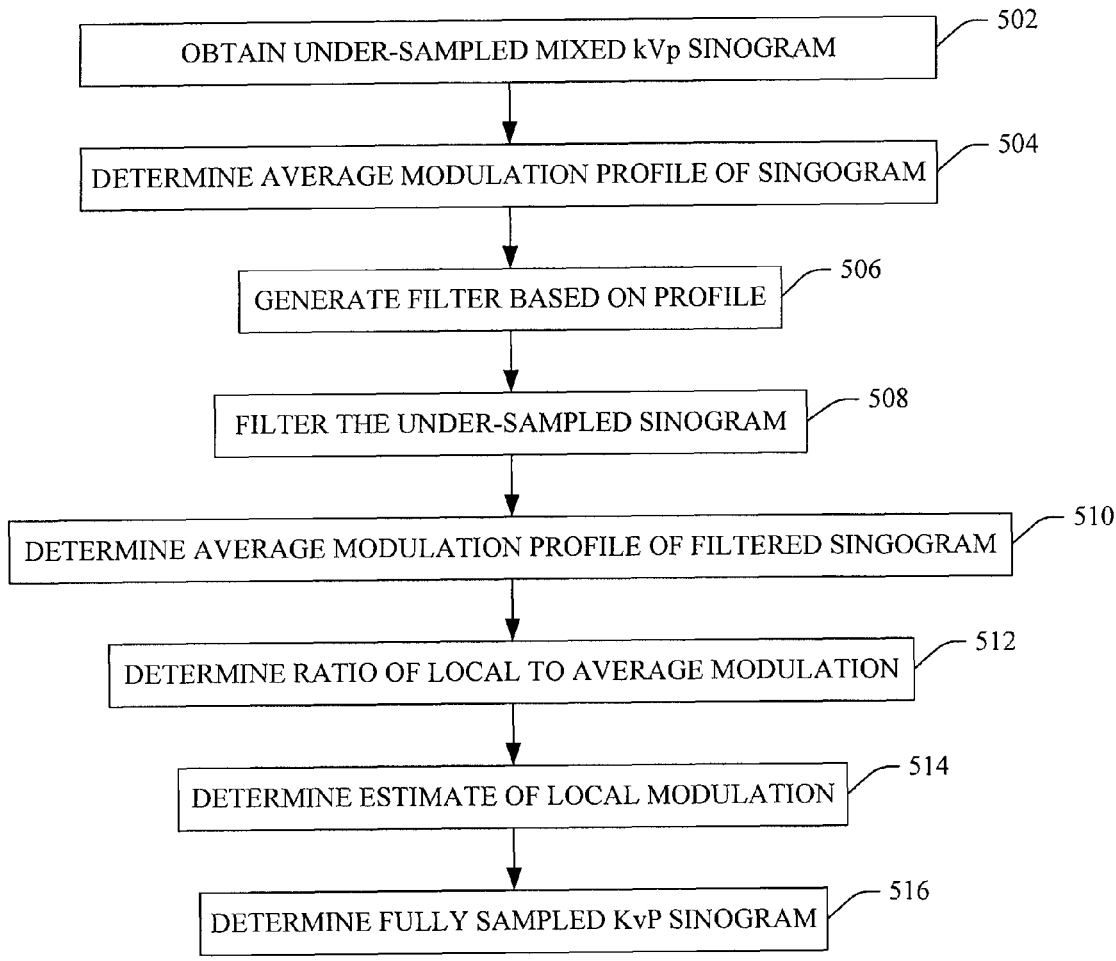
Figure 6:
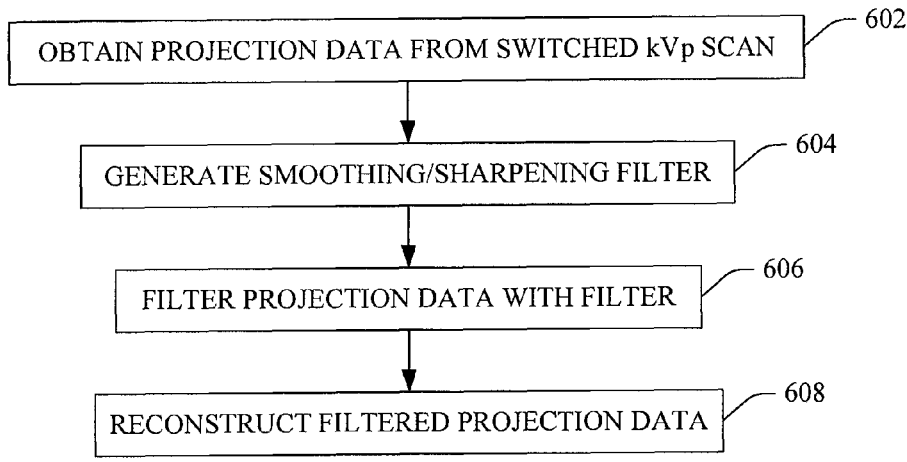

FIG. 1 illustrates an imaging system in connection with a fixe d kVp sinogram extractor and a de-noiser.
FIG. 2 shows an example fixed kVp sinogram extractor.
FIG. 3 illustrates an example modulation cycle.
FIG. 4 shows an example de-noiser.
FIG. 5 illustrates an example method for extracting a fully sampled fixed kVp sinogram from an under-sampled mixed kVp sinogram.
FIG. 6 illustrates an example method for de-noising a fully sampled fixed kVp sinogram extracted from an under-sampled mixed kVp sinogram and/or the under-sampled mixed kVp sinogram.

FIG. 1 illustrates an imaging system such as a computed tomography (CT) scanner 100. The scanner 100 includes a stationary gantry 102 and a rotating gantry 104, which is rotatably supported by the stationary gantry 102. The rotating gantry 104 rotates around an examination region 106 about a longitudinal or z-axis.

A radiation source 108, such as an x-ray tube, is supported by and rotates with the rotating gantry 104 around the examination region 106. The radiation source 108 emits radiation that traverses the examination region 106. A tube voltage controller 110 controls the voltage across to the radiation source 108 and hence the emission spectrum of the radiation source 108. The illustrated tube voltage controller 110 is configured to switch the radiation source 108 voltage between at least two different peak voltages during scanning. By way of non-limiting example, in one instance the tube voltage controller 110 is configured to switch the source voltage between 80 kVp and 140 kVp (or other desired spectral difference). The tube voltage controller 110 can employ a slow kV-switching algorithm (e.g., on the order of a few milliseconds) or fast kV-switching algorithm (e.g., for sub-millisecond cycles times).

A radiation sensitive detector array 112 detects radiation that traverses the examination region 106 and generates a sinogram of x-ray attenuation coefficient line integrals (projection data) indicative of the detected radiation. For multi-kVp data acquisitions, the projection data includes under-sampled mixed kVp line integrals for each different kVps.

A projection data processor 118 processes the line integrals. In the illustrated embodiment, the projection data processor 118 at least performs a kVp dependent water-based beam hardening correction on the corresponding line integrals. Different and/or other processing is also contemplated herein.

A fixed kVp extractor 120 determines a fully sampled kVp sinogram in different fixed kVp values from the processed under-sampled mixed kVp sinogram. As described in greater detail below, the fixed kVp extractor 120 consider the under sampled measured mixed kVp sinogram as a sum of a fully sampled fixed kVp sinogram in different kVp values and a local kVp modulation sinogram (e.g., from a minimum kVp to a maximum kVp), and extracts the fully sampled kVp sinogram in the different fixed kVp values based on the under-sampled mixed kVp sinogram and an estimate of a local kVp modulation sinogram.

A de-noiser 122 de-noises sinograms, including the under sampled mixed kVp sinogram and/or the extracted fully sampled fixed kVp sinogram. As described in greater detail below, in one instance this includes smoothing the lower kVp measurements and/or sharpening the higher kVp measurements of a sinogram to reduce noise while preserving a same average spatial resolution. This may facilitate mitigating reduced dose utility due to the variation of photon statistics between integration periods at lower and higher kVps with no tube current modulation.

According to the first aspect, a reconstructor 124 reconstructs the fully sampled kVp sinograms in the different fixed kVp values and generates volumetric image data using a suitable multi-energy reconstruction algorithm. The resulting image data generally will have less image streak artifacts relative to a configuration in which the reconstructor 124 reconstructs the under-sampled projection data. Additionally or alternatively, a spectral separation can be performed in the image domain, for example, for separating materials, such as tissue, contrast agent, etc. Spectral separation can also be performed in the projection domain by decomposing the fully sampled projection data into a plurality of basis materials.

A patient support 126, such as a couch, supports a patient in the examination region 106 and is movable along the z-axis in coordination with the rotation of the rotating gantry 104 to facilitate helical, axial, or other desired scanning trajectories.

A general purpose computing system serves as an operator console 128, and includes an output device such as a display and an input device such as a keyboard, mouse, and/or the like. Software resident on the console 126 allows the operator to control the operation of the system 100, for example, allowing the operator to select a multi-kVp switching data acquisition, a multi-kVp reconstruction algorithm, a projection and/or image domain spectral separation algorithm, etc.

It is to be appreciated that the fixed kVp determiner 120 and/or the de-noiser 122 can be implemented by one or more processors executing one or more computer readable instructions encoded on computer readable storage medium such as physical memory. Additionally or alternatively, the instructions may be included in a signal or carrier wave. The processor(s) and/or the storage medium can be part of the console 128 and/or one or more computing systems such as one or more computers.

In another embodiment, the fixed kVp determiner 120 is omitted. In yet another embodiment, the de-noiser 122 is omitted.

FIG. 2 illustrates an example of the fixed kVp sinogram extractor 120.

An average modulation determiner 202 determines an average modulation profile of attenuation line integrals of the under sampled measured mixed kVp sinogram. In this example, the average modulation determiner 202 determines an average modulation profile over a single modulation cycle of the under sampled measured mixed kVp sinogram.

FIG. 3 shows an example switching cycle for switching the x-ray tube voltage between 80 kVp and 140 kVp, in which a y-axis 302 represents tube voltage and an x-axis 304 represents reading or measurements 306 within a plurality of switching cycles 308. In the illustrate example, each switching cycle 308 consists of twelve (12) readings 306, and the average modulation profile is obtained by averaging the modulating cycle of line integrals over all cycles 308 of the three dimensional sinogram.

Returning to FIG. 2, a filter 204 convolves the under sampled measured mixed kVp sinogram with a one dimensional (1D) finite impulse response (FIR) filter oriented along the integration period (IP) axis. In a non-limiting instance, the filter 204 can be multiplied by low-pass 2D FIR filter along the plane of detector pixels to reduce the noise of the convolved sinogram. In this example, the 1D filter 204 is tailored based on the average modulation profile. Generally, the role of the filter is to isolate and emphasize the average modulation profile.

An average convolved modulation determiner 206 determines an average modulation profile of the convolved sinogram. In this example, this is achieved in a manner substantially similar to that described above in connection with the average modulation determiner 202.

A local modulation to average sinogram determiner 208 determines a sinogram of the local modulation strength of the convolved sinogram relative to the average of the convolved sinogram.

The local modulation to average sinogram determiner 208 includes a scale determiner 210 that determines a ratio of the modulation in a cycle to the average modulation. For this, for each reading in the convolved sinogram, a one dimensional (1D) profile of readings oriented along the integration period (IP) axis, having a length of one cycle and centered at the reading, is compared with the average modulation profile of the convolved sinogram.

In this example, the scale determiner 210 determines the ratio (scale) based on EQUATION 1:

$$\text{scale} = \frac{\sum_i x(i)^2}{\max\left(0, \sum_i x(i) \cdot y(i)\right)} \quad \text{EQUATION 1}$$

wherein x represents the bin number within a cycle of the convolved sinogram, and y represents the bin number within a cycle of the averaged convolved sinogram.

The local modulation to average sinogram determiner 208 also includes a correlation coefficient determiner 212 that determines a correlation coefficient that indicates how much a change in reading values in the original under sampled sinogram, in the vicinity of the selected reading, is caused due to the kVp modulation, and not due to structure variation.

In this example, the correlation coefficient determiner 212 determines the correlation coefficient (cor) as shown in EQUATION 2:

$$cor = \frac{\left(\max\left(0, \sum_i x(i) \cdot y(i)\right)\right)^2}{\left(\sum_i x(i)^2\right) \cdot \left(\sum_i y(i)^2\right)} \quad \text{EQUATION 2}$$

wherein, again, x represents the bin number within a cycle of the convolved sinogram, and y represents the bin number within a cycle of the averaged convolved sinogram.

The local modulation to average sinogram determiner 208 determines the sinogram of the local modulation strength of the convolved sinogram relative to the average of the convolved sinogram as the product of cor and scale (i.e., cor·scal).

A local modulation estimator 214 estimates a local kVp modulation of the non-convolved data based on the average modulation profile for the non-convolved data determined by the average modulation determiner 202 and the sinogram of the local modulation strength of the convolved sinogram relative to the average of the convolved sinogram (or cor·scal) determined by the local modulation to average sinogram determiner 208.

In this example, the local modulation estimator 214 estimates the local modulation in the sinogram due to the kVp modulation (local oscillation amplitude (non-convolved)) based on EQUATION 3:

$$\frac{\text{local oscillation amplitude}}{\text{average oscillation amplitude}} = cor \cdot scal, \quad \text{EQUATION 3}$$
$$\text{(non-convolved)}$$
$$\text{(non-convolved)}$$

wherein average oscillation amplitude (non-convolved) is the amplitude of the average modulation profile for the non-convolved data determined by the average modulation determiner 202.

A fixed kVp sinogram determiner 216 determines a fully sampled fixed kVp sinogram based on the under sampled measured mixed kVp sinogram and the estimate of the local modulation in the sinogram due to the kVp modulation determined by the local modulation estimator 214. In the illustrated embodiment, the fixed kVp sinogram determiner 216 subtracts the local modulation from the measured sinogram to determine the fully sampled fixed kVp sinogram. The fixed kVp sinogram can have any value within the range between the minimum and maximum kVp values (e.g., between 80 kVp and 140 kVp), and a particular kVp can be selected by varying the reference level of the modulation component.

Knowing the tube spectra at kVp levels out of this range, the average modulation profile can be extended beyond this range either by extrapolation from the measured profile, or independently, beyond the range. This way the fixed kVp sinogram can have values beyond the range between the minimum and maximum scan kVp values by selecting the reference level out of this range.

FIG. 4 illustrates an example of the de-noiser 122.

A smoothing/sharpening filter 402 convolves the under sampled mixed kVp sinogram and/or the fully sampled fixed kVp sinogram with a set of finite impulse response (FIR) filters, tailored for readings of different kVp values. For integration periods (IP) that fall within transitions, the original kVp value is replaced with an average kVp value before convolving.

A filter generator 404 generates the set of filters. In this embodiment, the filter generator 404 generates a set of filters associated with all the original kVp that smoothes measurements corresponding to lower kVp and enhances (sharpens) measurements corresponding to higher kVp.

A suitable set of filters preserves a same average spatial resolution, which can be achieved by forcing the average over the modulation cycle to be equal or substantially the same as a predetermine operator such as the Identity operator, which allows the enhancement and the smoothing of the different filters in the set to cancel each other out.

The following provides a non-limiting example of such filtering.

Let $p_{m0,n0,f0}$ stand for the original reading of detector column m0, detector column n0 and integration period (IP) f0. The corresponding reading obtained after convolving the sinogram with an enhancing or smoothing kernel can be determined as shown in EQUATION 4:

$$p^c_{m0,n0,f0} = \sum_{m=-M}^{M} \sum_{n=-N}^{N} \sum_{f=-F}^{F} p_{m0+m,n0+n,f0+f} \cdot K_{f0,m,n,f}, \quad \text{EQUATION 4}$$

wherein c represents the convolved sinogram, and $K_{f0}$ represents the convolution kernel that is enhancing or smoothing depending on the kV of the IP f0.

In terms of the number of integration periods (IP) per cycle (NIP) $K_{f0,m,n,f}$ satisfies the requirement shown in EQUATION 5:

$$\sum_{f0=1}^{NIP} K_{f0,m,n,f} \approx NIP \cdot \delta_{m,0} \cdot \delta_{n,0} \cdot \delta_{f,0}, \quad \text{EQUATION 5}$$

A non-limiting approach to select $K_{\{f0\}}$, which aims to reduce the variance of the convolved readings, averaged over the switching cycle, is based on EQUATION 6:

$$K_{\{f0\}} = \min_{k_{\{f0\}}} \text{var}_{nc}(k_{\{f0\}}), \quad \text{EQUATION 6}$$

$$\text{var}_{nc}(k_{\{f0\}}) = \frac{1}{NIP} \cdot \sum_{f0=1}^{NIP} \text{var}(p^c_{m0,n0,f0}(k_{f0})),$$

$$\text{var}(p^c_{m0,n0,f0}(k_{f0})) =$$

$$\sum_{m=-M}^{M} \sum_{n=-N}^{N} \sum_{f=-F}^{F} \text{var}(m0, n0, f0+f) \cdot K^2_{f0,m,n,f},$$

wherein var(m,n,f) represents the local noise variance of the non-convolved readings of IP f.

Generally, the relationship between values of var(m,n,f) of neighbor readings with different IP f is maintained approximately the same throughout the whole sinogram. For example, the ratio between var(f) for f of 140 kV and for f of 80 kV is about 0.17±0.02 throughout the whole sinogram. The term var($p^c_{m0,n0,f0}(k_{f0})$) in (3) stands for the noise variance of the convolved reading $p^c_{m0,n0,f0}$.

Due to noise cross-correlation between the filtered readings, the magnitude of var$_{nc}(k_{\{f0\}})$ correlates only partially to the local contribution of the sinogram to the image noise. Nevertheless, in general, selecting a set $K_{\{f0\}}$ that reduces this term leads to a considerable image noise reduction. A non-limiting approach to reducing var$_{nc}$ is by equalizing var($p^c_{m0,n0,f}$) for all IP f within the cycle as shown EQUATION 7:

$$\text{var}(p^c_{m0,n0,f0}(K_{f0})) = \text{const}, f0 \in 1:NIP. \quad \text{EQUATION 7:}$$

The following provides a non-limiting example of how to build the set $K_{\{f0\}}$ according EQUATION 4 for the switching cycle shown in FIG. 3.

Let var(kV) stand for the noise variance of the readings at some kV divided by the noise variance of their neighbors belonging to the 80 kV IP. As an example, for kVps of 80, 95, 125, and 140, this renders var(80)=1; var(95)=0.48; var(125)=0.22; and var(140)=0.17.

For a set of 3×3×3 kernels (i.e., N=M=F=1) (EQUATION 4), EQUATION 8 can be used:

$$K_{f0,m,n,f} = (-(\delta_{m,-1} + \delta_{m,1}) \cdot \alpha(f0) + \delta_{m,0} \cdot (1 + 2 \cdot \alpha(f0))) \cdot \quad \text{EQUATION 8}$$
$$\ldots \cdot (-(\delta_{n,-1} + \delta_{n,1}) \cdot \alpha(f0) + \delta_{n,0} \cdot (1 + 2 \cdot \alpha(f0))) \cdot$$
$$\ldots \cdot (-(\delta_{f,-1} + \delta_{f,1}) \cdot \alpha(f0) + \delta_{f,0} \cdot (1 + 2 \cdot \alpha(f0))).$$

For the given switching cycle, the parameters α(f0) that equalize var($p^c_{m0,n0,f}$) are denoted by: α(f0=2)=α(f0=3)=α(f0=4)=α(f0=5)≈α$_1$, α(f0=1)=α(f0=6)≈α$_2$, α(f0=7)=α(f0=12)≈α$_3$, α(f0=8)=α(f0=11)≈α$_4$, and α(f0=9)=α(f0=10)≈α$_5$.

Equalizing var($p^c_{m0,n0,f}$) (EQUATION 7) defines well together with EQUATIONS 7 and 8 the relations between the different $\alpha_i$. In other words, for each value of one of the $\alpha_i$, the values of the remaining $\alpha_i$ are determined automatically by EQUATIONS 6-8.

Various approaches can be used to solve $\alpha_i$. With one approach, $\alpha_1$ is first assigned an initial value. Then, $\alpha_i(\alpha_1)$ is calculated for $i \in 2:5$, using EQUATIONS 6-8. Then, the average kernel $$\frac{1}{NIP} \cdot \sum_{f0=1}^{NIP} K_{f0,m,n,f}$$

is calculated. If the average kernel is smoothing (sharpening), $\alpha_1$ is correspondingly increased (decreased), and $\alpha_i(\alpha_1)$ and $$\frac{1}{NIP} \cdot \sum_{f0=1}^{NIP} K_{f0,m,n,f}$$

are calculated again. This process continues unless or until EQUATION 5 is satisfied.

In the non-limiting example illustrated herein, performing the above results in $\alpha_1 = 0.0357$. The corresponding average filter in EQUATION 9 is about equal practically to the identity filter.

$$\frac{1}{NIP} \cdot \sum_{f0=1}^{NIP} K_{f0,m,n,f} = \begin{cases} \delta_{m,0} + \delta_{n,0} + \delta_{f,0} = 3 \Rightarrow 1 \\ \delta_{m,0} + \delta_{n,0} + \delta_{f,0} = 2 \Rightarrow -0.0055 \\ \delta_{m,0} + \delta_{n,0} + \delta_{f,0} = 3 \Rightarrow 0.0026 \\ \delta_{m,0} + \delta_{n,0} + \delta_{f,0} = 4 \Rightarrow 0.0002. \end{cases} \quad \text{EQUATION 9}$$

In one non-limiting instance, by using EQUATIONS 4 and 8 with 0.0357 For $\alpha_1$, patient dose is decreased by about 24% for the same image noise level and spatial resolution of the image reconstructed from the unfiltered under-sampled sinogram of mixed kVp readings. As such, the additional 46% of patient dose required for the kVp-switching scan is now shrunk to about 11%.

Although the de-noiser 122 has been discussed above in connection with the under sampled measured fixed kVp sinogram, it is to be appreciated the de-nosier 122 can additionally or alternatively be used to filter the fully sampled fixed kVp sinogram extracted by the fixed kVp sinogram extractor. Likewise, the de-noised sinogram will improve dose utility relative to the unfiltered fully sampled fixed kVp sinogram. In this case, the values for var(kV) for each reading can be taken according to the original kV values of the under-sampled sinogram of mixed kVp readings.

FIG. 5 illustrates an example method for extracting a fully sampled fixed kVp sinogram from an under-sampled mixed kVp sinogram.

It is to be appreciated that the ordering of the acts in the methods described herein is not limiting. As such, other orderings are contemplated herein. In addition, one or more acts may be omitted and/or one or more additional acts may be included.

At 502, an under-sampled mixed kVp sinogram from a switched kVp CT scan is obtained.

At 504, an average modulation profile of the under-sampled mixed kVp sinogram is determined.

At 506, a filter is generated based on the average modulation profile.

At 508, the under-sampled mixed kVp sinogram is convolved with the filter.

At 510, an average modulation profile of the convolved sinogram is determined.

At 512, a ratio of a local modulation strength/amplitude to an average sinogram is determined based on the convolved under-sampled mixed kVp sinogram and the average modulation profile of the convolved sinogram.

At 514, an estimate of the local kVp modulation is determined based on the average modulation profile of the under-sampled mixed kVp sinogram and the ratio obtained by 512.

At 516, a fully sampled fixed kVp sinogram for a kVp of interest is determined based on the under-sampled mixed kVp sinogram and the estimate.

An anatomical image at a single kVp is reconstructed or a spectral separation, in the projection and/or image domain, is performed.

FIG. 6 illustrates an example method for de-noising a switched kVp sinogram.

It is to be appreciated that the ordering of the acts in the methods described herein is not limiting. As such, other orderings are contemplated herein. In addition, one or more acts may be omitted and/or one or more additional acts may be included.

At 602, projection data from a switched kVp CT scan is obtained.

At 604, a de-noising filter that smoothes lower kVp measurements and sharpens higher kVp measurements is generated.

At 606, the projection data is filtered with the de-noised filter.

At 608, the projection data is reconstructed, producing de-noised image data.

The above may be implemented by way of computer readable instructions, which when executed by a computer processor(s), cause the processor(s) to carry out the described acts. In such a case, the instructions are stored in a computer readable storage medium associated with or otherwise accessible to the relevant computer. The acts need not be performed concurrently with data acquisition.

The invention has been described herein with reference to the various embodiments. Modifications and alterations may occur to others upon reading the description herein. It is intended that the invention be construed as including all such modifications and alterations insofar as they come within the scope of the appended claims or the equivalents thereof.

What is claimed is:

1. A method, comprising:
   generating an estimate of a local kVp modulation profile based on an under-sampled mixed kVp sinogram generated from a switched kVp computed tomography scam; and
   extracting a fully sampled fixed kVp sinogram for a predetermined kVp of interest from the under-sampled mixed kVp sinogram generated from the switched kVp computed tomography scan by subtracting the estimate from the under-sampled mixed kVp sinogram.

2. The method of claim 1, further comprising:
   generating an average kVp modulation profile of a length of a switching cycle by folding together one dimensional cycle segments of the under-sampled mixed kVp sinogram; and
   generating a ratio of a local modulation profile amplitude to an amplitude of the average modulation profile.

3. The method of claim 2, wherein the under-sampled mixed kVp sinogram includes a two or three dimensional array of a plurality of modulation cycles, and further comprising:
generating the average kVp modulation profile by averaging the plurality of modulation cycle over a modulation cycle to generate a single average modulation cycle.

4. The method of claim 2, further comprising:
generating a convolved sinogram by convolving the under-sampled mixed kVp sinogram with a convolution kernel tailored to detect the kVp modulation; and
generating an average of the convolved kVp sinogram by averaging the convolved sinogram over the modulation cycle to generate a single average convolved profile of the length of the switching cycle; and
generating the ratio between a local amplitude of the profile along one switching cycle of the convolved sinogram and an amplitude of the average convolved profile.

5. The method of claim 4, further comprising:
generating a local signal ratio indicative of a ratio of between a local profile amplitude of the convolved sinogram and the amplitude of the average convolved profile;
generating a correlation coefficient indicative of a correlation between the local profile and the average profile of the convolved sinogram; and
multiplying the local signal ratio by the local correlation coefficient.

6. The method of claim 5, further comprising:
generating the signal ratio for each reading, taking a cycle that surrounds the reading and calculating, by least squares, a ratio before multiplying the ratio with the correlation coefficient.

7. The method of claim 5, further comprising:
estimating the local kVp estimate based on the average non-convolved modulation profile and the local signal ratio.

8. The method of claim 1, wherein the switched kVp computed tomography scan has a lower dose than a corresponding fixed kVp computed tomography scan.

9. The method of claim 1, further comprising:
de-noising at least one of the fully sampled fixed kVp sinogram or the under-sampled mixed kVp sinogram.

10. The method of claim 9, further comprising:
de-noising the at least one of the fully sampled fixed kVp sinogram or the under-sampled mixed kVp sinogram by smoothing lower kVp measurements of the sinograms and sharpening higher kVp measurements of the sinograms.

11. The method of claim 10, further comprising:
minimizing a local noise of the sinogram readings averaged over one switching cycle.

12. The method of claim 10, wherein a noise level for different kVp line integrals is substantially the same due to the smoothing and sharpening.

13. The method of claim 9, wherein a noise of the extracted fully sampled sinograms readings before smoothing and sharpening is estimated based on a noise of the corresponding under-sampled mixed kVp sinogram readings.

14. The method of claim 9, wherein an average spatial resolution for the de-noised sinogram is about the same as an average resolution corresponding to the non de-noised sinogram.

15. A system, comprising:
an average modulation determiner that determines an average modulation profile over a modulation cycle of an under-sampled mixed kVp sinogram from a switched kVp computed tomography scan;
a local modulation amplitude to average modulation amplitude determiner that determines a local modulation amplitude to average modulation amplitude ratio profile based on a convolved under-sampled mixed kVp sinogram and an average of the convolved under-sampled mixed kVp sinogram;
a local modulation estimator estimates a local modulation based on the average modulation profile and the local modulation amplitude to average modulation amplitude ratio profile; and
a fixed sinogram extractor that extracts a fully sampled fixed kVp sinogram from the under-sampled mixed based on the under-sampled mixed kVp sinogram and the local modulation estimate.

16. The system of claim 15, the fixed sinogram extractor comprising:
generating the fixed kVp sinogram by subtracting the local modulation estimate from the under-sampled mixed kVp sinogram.

17. The system of claim 15, further comprising:
a de-noiser that de-noises at least one of the fully sampled fixed kVp sinogram or the under-sampled mixed kVp sinogram.

18. The system of claim 15, further comprising:
tube voltage controller that switches a voltage of a radiation source of the system between two different voltages range from 80 kVp to 140 kVp.

19. The system of claim 18, wherein the fully sampled fixed kVp sinogram is either within or outside this kVp range.

20. The system of claim 15, wherein the switched kVp computed tomography scan has a lower dose than a corresponding fixed kVp computed tomography scan generating a corresponding fully sampled fixed kVp sinogram.

21. The system of claim 20, wherein the fixed kVp computed tomography scan is performed at a highest of the switched kVps.

22. The system of claim 15, wherein the fixed sinogram extractor allows for reducing dose relative to fixed kVp computed tomography scan.

23. A method, comprising:
de-noising at least one of a fully sampled fixed kVp sinogram extracted from an under-sampled mixed kVp sinogram or the under-sampled mixed kVp sinogram by smoothing lower kVp measurements of the sinograms and sharpening higher kVp measurements of the sinograms.

24. The method of claim 23, wherein a noise level for different kVp line integrals is substantially the same and an average spatial resolution for the de-noised sinogram is about the same as an average resolution corresponding to the non de-noised sinogram.

25. The method of claim 23, further comprising:
generating an estimate of a local kVp modulation sinogram based on the under-sampled mixed kVp sinogram; and
extracting the fully sampled fixed kVp sinogram by subtracting the estimate from the under-sampled mixed kVp sinogram.

26. A method, comprising:
extracting a fully sampled fixed kVp sinogram for a predetermined kVp of interest from an under-sampled mixed kVp sinogram generated from a switched kVp computed tomography scan, wherein the switched kVp computed tomography scan has a lower dose than a corresponding fixed kVp computed tomography scan.

27. The method of claim 23, wherein the under-sampled mixed kVp sinogram is generated from a switched kVp computed tomography scan, and the switched kVp computed tomography scan has a lower dose than a corresponding fixed kVp computed tomography scan generating a corresponding fully sampled fixed kVp sinogram.

28. The method of claim 23,
- de-noising at least one of a fully sampled fixed kVp sinogram extracted from an under-sampled mixed kVp sinogram or the under-sampled mixed kVp sinogram by smoothing lower kVp measurements of the sinograms and sharpening higher kVp measurements of the sinograms,
- wherein the fully sampled fixed kVp sinogram is extracted for a pre-determined kVp of interest and the under-sampled mixed kVp sinogram is generated from a switched kVp computed tomography scan, and
- wherein an average spatial resolution of the de-noised sinogram is about the same as an average resolution corresponding to the non-de-noised sinogram.

* * * * *